US008877017B2

(12) United States Patent
Nakaya et al.

(10) Patent No.: US 8,877,017 B2
(45) Date of Patent: Nov. 4, 2014

(54) METHOD FOR SEPARATING HEXAFLUOROPROPYLENE OXIDE FROM HEXAFLUOROPROPYLENE

(75) Inventors: Hideki Nakaya, Osaka (JP); Kazuyoshi Ichihara, Osaka (JP); Yasuhide Senba, Osaka (JP); Mikio Nakagoshi, Osaka (JP); Kazunori Morimoto, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 543 days.

(21) Appl. No.: 13/256,949

(22) PCT Filed: Feb. 18, 2010

(86) PCT No.: PCT/JP2010/052404
§ 371 (c)(1), (2), (4) Date: Sep. 16, 2011

(87) PCT Pub. No.: WO2010/106865
PCT Pub. Date: Sep. 23, 2010

(65) Prior Publication Data

US 2012/0006672 A1 Jan. 12, 2012

(30) Foreign Application Priority Data

Mar. 18, 2009 (JP) ............................. P 2009-065633

(51) Int. Cl.

| | |
|---|---|
| ***B01D 3/40*** | (2006.01) |
| ***C07C 17/386*** | (2006.01) |
| ***C07C 21/18*** | (2006.01) |
| ***C07D 301/32*** | (2006.01) |
| ***C07D 303/08*** | (2006.01) |

(52) U.S. Cl.
CPC . *C07C 21/18* (2013.01); *B01D 3/40* (2013.01); *C07C 17/386* (2013.01); *C07D 301/32* (2013.01); *C07D 303/08* (2013.01)
USPC ............... 203/67; 203/80; 549/541; 570/170; 570/178

(58) Field of Classification Search
USPC ........... 203/50, 67, 73, 80; 549/541; 570/170, 570/178
See application file for complete search history.

(56) References Cited

U.S. PATENT DOCUMENTS 4,134,796 A * 1/1979 Oda et al. ........................ 203/63
4,902,810 A * 2/1990 Ikeda et al. .................. 549/521

(Continued)

FOREIGN PATENT DOCUMENTS

CN 101367778 A 2/2009
JP 09-020765 A 1/1997

(Continued)

OTHER PUBLICATIONS

International Preliminary Report on Patentability for PCT/JP2010/052404 dated Oct. 18, 2011.

(Continued)

*Primary Examiner* — Virginia Manoharan
(74) *Attorney, Agent, or Firm* — Birch, Stewart, Kolasch & Birch, LLP

(57) ABSTRACT

The present invention provides a novel method for separating hexafluoropropylene oxide (HFPO) from hexafluoropropylene (HFP), which is capable of reducing the burden on the environment. A mixture including HFPO and HFP is subjected to an extractive distillation operation using, as a solvent, at least one of a fluorine-containing saturated compound represented by the general formula $C_nH_aF_b$ (wherein n, a and b are integers which satisfy: n=3 to 8, $0 \le a \le 2n+1$, and $1 \le b \le 2n+2$) thereby separating into a first fraction including HFPO and a second fraction including HFP and the solvent. At least one of 1-bromopropane and 2-bromopropane may be u as the solvent in place of the fluorine-containing saturated compound.

5 Claims, 1 Drawing Sheet

(56) References Cited

U.S. PATENT DOCUMENTS

| | | | | |
|---|---|---|---|---|
| 7,405,312 | B2 * | 7/2008 | Lee et al. | 549/520 |
| 2007/0249877 | A1 * | 10/2007 | McDonald et al. | 570/178 |
| 2010/0016615 | A1 | 1/2010 | Nakaya et al. | |
| 2010/0105932 | A1 * | 4/2010 | Ramjugernath et al. | 549/541 |
| 2010/0187464 | A1 * | 7/2010 | Knapp et al. | 252/2 |

FOREIGN PATENT DOCUMENTS

| | | | |
|---|---|---|---|
| JP | 3785652 | B | 1/1997 |
| JP | 09-136882 | A | 5/1997 |
| WO | WO 2008/050760 | A1 | 5/2008 |

OTHER PUBLICATIONS

Hongli et al., "Purification Method of Hexafluoropropylene", Chemical Production and Technology, 2005, pp. 7-8 with English Translation.

* cited by examiner

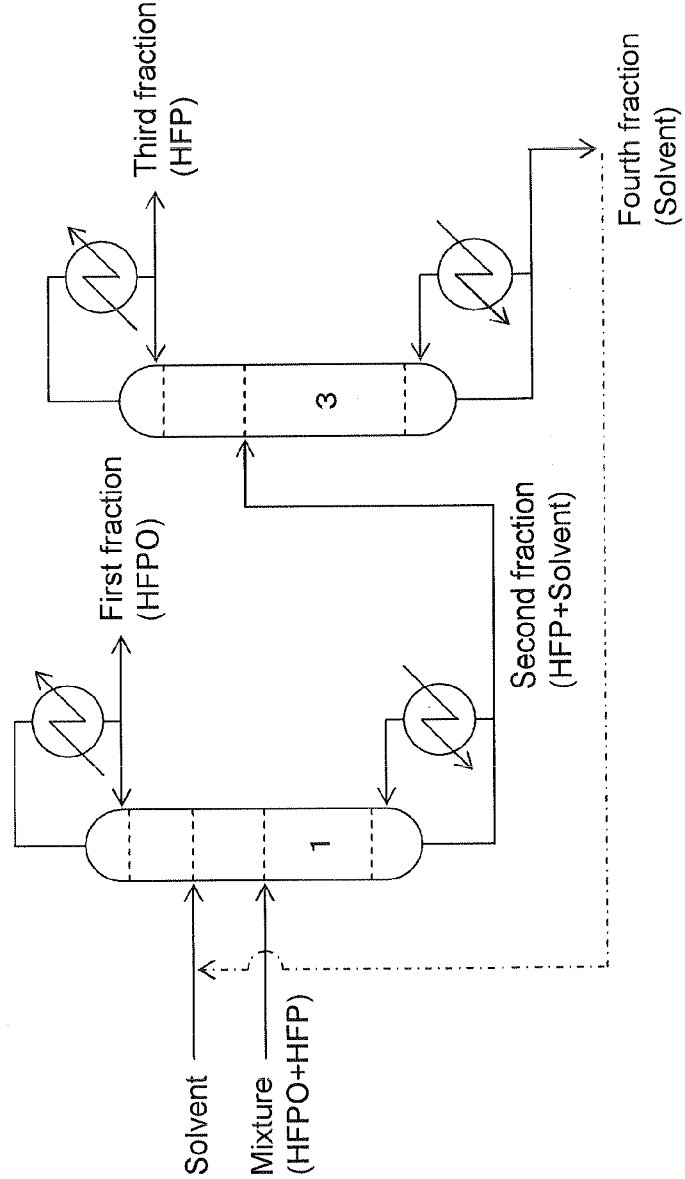
Solvent
Mixture (HFPO+HFP)
1
First fraction (HFPO)
Second fraction (HFP+Solvent)
3
Third fraction (HFP)
Fourth fraction (Solvent)

METHOD FOR SEPARATING HEXAFLUOROPROPYLENE OXIDE FROM HEXAFLUOROPROPYLENE

CROSS REFERENCE

The present application is a national phase under 35 U.S.C. §371 of International Application No. PCT/JP2010/052404, filed on Feb. 18, 2010. Priority is also claimed to Japanese Application No. 2009-065633 filed on Mar. 18, 2009. The entire contents of each of these applications are hereby incorporated by reference.

TECHNICAL FIELD

The present invention relates to a method for separating hexafluoropropylene oxide (hereinafter also referred to as HFPO) from hexafluoropropylene (hereinafter also referred to as HFP), and more particularly to a method for obtaining hexafluoropropylene oxide from a mixture of hexafluoropropylene oxide and hexafluoropropylene.

BACKGROUND ART

Hexafluoropropylene oxide is an important compound in the production of fluorine-containing compounds, since it is used, for example, as a raw material for perfluorovinyl ether. An oligomer of the hexafluoropropylene oxide is utilized as a lubricating oil, a heating medium and the like.

Generally, hexafluoropropylene oxide is produced by using hexafluoropropylene as a raw material and oxidizing the hexafluoropropylene according to various methods (see, for example, Patent Literature 1).

The reaction mixture obtained in such a production method contains HFPO as the objective product, and the unreacted HFP. It is preferable to purify the reaction mixture to obtain high purity HFPO, and it is also preferable to recover the unreacted HFP to reuse it as a raw material for the production of HFPO.

Distillation is generally utilized for purification. However, boiling points of HFP and HFPO are −29.4° C. and −27.4° C. (both under the atmospheric pressure), respectively. Due to closeness of the boiling points, it is difficult to separate them from each other by distillation. There is proposed a method in which distillation is performed at a low temperature under a low pressure (see Patent Literature 2). However, there is a drawback that a relative volatility cannot be sufficiently increased even by such a method.

Therefore, extractive distillation is utilized so as to separate HFPO from a mixture of HFP and HFPO (see Patent Literatures 1 and 3).

It is known that this extractive distillation may use, as a solvent, a chlorine-containing compound represented by the following general formula (Y):

$$C_{n'}H_{a'}Cl_{b'}F_{c'} \quad (Y)$$

wherein n', a', b' and c' are integers which satisfy: n'=2 to 6, $1 \le a' \le n+1$, $1 \le b' \le 2n$, $1 \le c' \le 2n$, and a'+b'+c'=2n+2.

Specific examples thereof include 1,1-dichloro-1-fluoroethane (HCFC-141b), 2,2-dichloro-1,1,1-trifluoroethane (HCFC-123), 1,2-dichloro-1,1,2-trifluoroethane (HCFC-123a), 3,3-dichloro-1,1,1,2,2-pentafluoropropane (HCFC-225ca) and 1,3-dichloro-1,1,2,2,3-pentafluoropropane (HCFC-225cb).

It is also known that the above extractive distillation may also use, as the solvent, chlorine-containing compounds such as $CH_2Cl_2$, $CHCl_3$, $CCl_4$ and $CH_2ClCH_2Cl$.

CITATION LIST

Patent Literature

Patent Literature 1: WO 2008/050760
Patent Literature 2: JP 9-136882 A
Patent Literature 3: JP 3785652 B

SUMMARY OF INVENTION

Technical Problem

However, the above-mentioned chlorine-containing compound may exerts adverse impact on environment. Particularly, the chlorine-containing compound represented by the above general formula (Y) may cause destruction of the ozone layer and, for example, 1,1-dichloro-1-fluoroethane (HCFC-141b) has an ozone depletion potential of about 0.1.

An object of the present invention is to provide a novel method for separating hexafluoropropylene oxide from hexafluoropropylene, which is capable of reducing the burden on the environment.

Solution to Problem

In order to separate hexafluoropropylene oxide (HFPO) from hexafluoropropylene (HFP) by extractive distillation, a solvent having a high relative volatility of HFPO to HFP is preferably used. Regarding a certain substance, however, it is impossible to anticipate its value of the relative volatility of HFPO to HFP, and it is very difficult to judge whether or not the substance can be used as the solvent for separation of HFPO from HFP by extractive distillation. The present inventors have intensively studied on various substances, and thus the present invention has been completed.

According to one aspect of the present invention, there is provided a method for separating hexafluoropropylene oxide from hexafluoropropylene, which comprises subjecting a mixture including hexafluoropropylene oxide and hexafluoropropylene to an extractive distillation operation using, as a solvent, at least one of a fluorine-containing saturated compound (hereinafter also may be simply referred to as a fluorine-containing compound) represented by the following general formula (X):

$$C_nH_aF_b \quad (X)$$

wherein n, a and b are integers which satisfy: n=3 to 8, $0 \le a \le 2n+1$, and $1 \le b \le 2n+2$, thereby separating into a first fraction including hexafluoropropylene oxide and a second fraction including hexafluoropropylene and the solvent.

A fluorine-containing compound containing no chlorine has never been studied as the solvent for extractive distillation since it has a small polarity as compared with a chlorine-containing compound. However, it was confirmed by the tests of the present inventors that the above fluorine-containing compound exhibits a high relative volatility of HFPO to HFP. According to the present invention, since HFPO is separated from a mixture including HFPO and HFP in the form of the first fraction by an extractive distillation operation using such a fluorine-containing compound as the solvent, thus obtained HFPO is able to have a purity at least higher than that of an original mixture, and also the burden on the environment can be reduced as compared with a conventional method using the chlorine-containing compound. Particularly, such a fluorine-containing compound has an advantage of generally exhibiting a small ozone depletion potential as compared with a chlorine-containing compound represented by the above general formula (Y).

The above fluorine-containing compound can have a boiling point not less than −5° C. and not more than 100° C. (under 0.1 MPa or an atmospheric pressure, hereinafter the same shall apply unless otherwise specified). The fluorine-containing compound having a boiling point not less than −5° C. has sufficiently higher boiling point than that of both HFPO and HFP, and is capable of efficiently separating them from each other by the extractive distillation operation. The fluorine-containing compound having a boiling point not more than 100° C. is capable of changing its state of a liquid phase into a vapor phase (steam) without requiring an excessively high temperature, and thus it can prevent decomposition of HFP and HFPO and also can decrease requisite amount of heat as small as possible.

The above fluorine-containing compound is a saturated compound. Such a fluorine-containing saturated compound may be either a non-cyclic compound (in the above general formula (X), n, a and b satisfy: a+b=2n+2) or a cyclic compound (in the above general formula (X), n, a and b satisfy: a+b=2n+2−m, and m represents the number of the ring structure).

The above fluorine-containing compound preferably contains hydrogen, that is, a so-called hydrofluorocarbon (HFC) (in the above general formula (X), a is an integer which satisfies: 1≤a≤2n+1). The hydrofluorocarbon has a feature of generally having a high polarity as compared with perfluorocarbon, so that it can dissolve a polar substance therein.

Such the hydrofluorocarbon can be selected from the group consisting of 1,1,1,3,3-pentafluoropropane ($CHF_2CH_2CF_3$: HFC-245fa), 1,1,1,3,3-pentafluorobutane ($CH_3CF_2CH_2CF_3$: HFC-365mfc), 1,1,1,2,2,3,4,5,5,5-decafluoropentane ($CF_3CHFCHFCF_2CF_3$: HFC-43-10mee) and 1,1,2,2,3,3,4-heptafluorocyclopentane (c-$CH_2CHFCF_2CF_2CF_2$: HFC-C-447ef). Any of these hydrofluorocarbons has an advantage of having an ozone depletion potential of zero.

However, the above fluorine-containing compound may be a so-called perfluorocarbon (PFC) which is hydrogen-free (in the above the general formula (X), a=0). The perfluorocarbon has a feature of having a low polarity as compared with hydrofluorocarbon, and having a very high stability.

Alternatively, in place of at least one of the fluorine-containing compound (fluorine-containing saturated compound) represented by the above general formula (X), it is also possible to use, as the solvent, at least one of 1-bromopropane and 2-bromopropane. That is, according to another aspect of the present invention, there is provided a method for separating hexafluoropropylene oxide from hexafluoropropylene, which comprises subjecting a mixture including hexafluoropropylene oxide and hexafluoropropylene to an extractive distillation operation using at least one of 1-bromopropane and 2-bromopropane as a solvent, thereby separating into a first fraction including hexafluoropropylene oxide, and a second fraction including hexafluoropropylene and the solvent.

Since 1-bromopropane and 2-bromopropane do not contain chlorine and therefore exhibit a small polarity as compared with the chlorine-containing compound, they have never been studied as the solvent for extractive distillation, heretofore. However, it was confirmed by the tests of the present inventors that 1-bromopropane and 2-bromopropane also exhibits a high relative volatility of HFPO to HFP. According to the present invention, since HFPO is separated from a mixture including HFPO and HFP in the form of the first fraction by an extractive distillation operation using at least one of 1-bromopropane and 2-bromopropane as the solvent, the burden on the environment can be reduced as compared with a conventional method using the chlorine-containing compound. Particularly, 1-bromopropane and 2-bromopropane have an advantage of a lower price and being comparatively easy to handle, and their use for a cleaning agent is accelerated, industrially.

Further, in place of at least one of the fluorine-containing compound (fluorine-containing saturated compound) represented by the above general formula (X), it is also possible to use, as the solvent, a fluorine-containing ether compound such as hydrofluoroether and perfluoroether. However, the fluorine-containing ether compound is less preferable since it exhibits a low relative volatility of HFPO to HFP as compared with the above fluorine-containing compound or 1-bromopropane and 2-bromopropane.

The method according to any aspect of the present invention may further comprise subjecting the second fraction obtained by the extractive distillation operation to a distillation operation thereby separating into a third fraction including hexafluoropropylene and a fourth fraction including the solvent. Therefore, it is possible to separate HFPO from a mixture including HFPO and HFP in the form of the first fraction, and also to separate HFP in the form of the third fraction. HFP thus separated and recovered can be utilized as a raw material for the production of HFPO from HFP. The solvent thus separated and recovered can be utilized as the solvent for the above extractive distillation operation.

The "mixture including hexafluoropropylene oxide and hexafluoropropylene" used in the present invention means that it substantially composed of HFPO and HFP, and may contain a small amount of other component(s). The proportion of such other component(s) in the mixture is, for example, about 10% by mole or less, preferably about 5% by mole or less, and more preferably from about 3 to 0% by mole.

In the present invention, the "fraction including . . . " means that it is substantially composed of the mentioned component(s) and may contain a small amount of other component(s). The proportion of such other component(s) varies depending on the above mixture used in the present invention and is, for example, about 20% by mole or less, preferably about 10% by mole or less, and more preferably from about 5 to 0% by mole.

Advantageous Effects of Invention

According to the present invention, there is provided a method for separating hexafluoropropylene oxide from hexafluoropropylene, which is a novel method capable of reducing the burden on the environment.

BRIEF DESCRIPTION OF DRAWINGS

FIG. 1 is a schematic view for explaining a method for separating hexafluoropropylene oxide (HFPO) from hexafluoropropylene (HFP) in an embodiment of the present invention.

DESCRIPTION OF EMBODIMENTS

The method for separating hexafluoropropylene oxide (HFPO) from hexafluoropropylene (HFP) in an embodiment of the present invention will be described in detail below.

First, a mixture including HFPO and HFP, and a solvent are prepared.

The mixture used in the present embodiment includes HFPO and HFP. There is no particular limitation on the mixing ratio of HFPO and HFP. For easier understanding, the present embodiment will be hereinafter described on the assumption that the mixture is composed of two components of HFPO and HFP. However, the present embodiment is not limited thereto, and the mixture may contain a small amount of other component(s).

Although there is no particular limitation on such the mixture, the mixture may be obtained by, for example, oxidizing HFP to form HFPO with the use of HFP as a raw material, and optionally subjecting a resultant reaction mixture to a post-treatment. In this case, the mixing molar ratio of HFPO and HFP is typically 1:about 0.1 to 9.

With respect to the solvent, the larger relative volatility of HFPO to HFP it has, the more preferable it is.

As such the solvent, it is possible to use at least one of a fluorine-containing compound represented by the following general formula (X):

$$C_nH_aF_b \quad (X)$$

wherein n, a and b are integers which satisfy: n=3 to 8, $0 \leq a \leq 2n+1$, and $1 \leq b \leq 2n+2$.

In order to use the fluorine-containing compound as the solvent, the boiling point thereof is preferably not less than −5° C. and not more than 100° C., and more preferably not less than 10° C. and not more than 90° C.

The above fluorine-containing compound is a fluorine-containing saturated compound, and may be either a non-cyclic compound or a cyclic compound. Particularly, hydrofluorocarbon (HFC) is preferably used, and examples thereof include 1,1,1,3,3-pentafluoropropane (HFC-245fa, boiling point of 15.3° C.), 1,1,1,3,3-pentafluorobutane (HFC-365mfc, boiling point of 40.2° C.), 1,1,1,2,2,3,4,5,5,5-decafluoropentane (HFC-43-10mee, boiling point of 55° C.) 1,1,2,2,3,3,4-heptafluorocyclopentane (HFC-C-447ef, boiling point of 82.5° C.) and the like.

Alternatively, 1-bromopropane (boiling point of 71° C.) and/or 2-bromopropane (boiling point of 59.4° C.) may be used as the solvent.

Such the solvent has a high relative volatility of HFPO to HFP, and does not exhibit azeotropic phenomenon with HFP and/or HFPO.

Next, referring to FIG. 1, the above-mentioned mixture (HFPO+HFP) and the solvent are supplied to an extractive distillation column 1 to subject the mixture of them to an extractive distillation operation. Generally, the supply section of the solvent is located above the supply section of the above mixture. In the extractive distillation column 1, an intervening part between these supply sections is a concentration section, and with respect to the concentration section an upper section is a solvent recovery section while a lower section is a recovery section.

Any of the above-mentioned solvent has a large affinity with HFP as compared with HFPO, and a volatility of HFP decreases by the addition of the solvent. Therefore, a first fraction including HFPO is discharged from the column top side of the extractive distillation column 1, while a second fraction including HFP and the solvent is discharged from the column bottom side thereof. Thus, HFPO is obtained in the form of the first fraction.

In the example shown in FIG. 1, the first fraction is obtained as a balance resulted by condensing a column top steam fraction in a condenser and refluxing a part of it to the extractive distillation column 1. The second fraction is obtained as a balance resulted by transferring a part of the column bottom liquid fraction to a reboiler, and the part transferred to the reboiler is vaporized by heating and returned to the extractive distillation column 1.

The conditions of the extractive distillation operation can be appropriately selected according to the solvent to be used, the target purity for HFPO in the first fraction and the like. For example, the supply molar ratio of the mixture and the solvent is 1:about 1 to 30, and preferably 1:about 5 to 15. In addition, for example, the temperature and the pressure in the extractive distillation column 1 may be about −5 to 150° C. and about 0.2 to 0.5 MPaG (gauge pressure). However, these are illustrative, and the present embodiment is not limited to these conditions.

Next, the second fraction (HFP+solvent) obtained from the extractive distillation column 1 is supplied to a solvent recovery column 3 and the second fraction is subjected to a distillation operation.

A third fraction including HFP is discharged from the column top side of the solvent recovery column 3, while a fourth fraction including the solvent is discharged from the column bottom side thereof. Thus, HFP is obtained in the form of the third fraction.

In the example shown in FIG. 1, the third fraction is obtained as a balance resulted by condensing a column top steam fraction in a condenser and refluxing a part of it to the solvent recovery column 3. The fourth fraction is obtained as a balance resulted by transferring a part of the column bottom liquid fraction to a reboiler, and the portion transferred to the reboiler is vaporized by heating and returned to the solvent recovery column 3.

The conditions of the distillation operation can be appropriately selected according to the solvent to be used, the target purity of for HFP in the third fraction and the like. For example, the temperature and the pressure in the solvent recovery column 3 may be about −5 to 150° C. and about 0.2 to 0.5 MPaG (gauge pressure). However, these are illustrative, and the present embodiment is not limited to these conditions.

As described above, HFPO is separated from the mixture including HFPO and HFP in the form of the first fraction and, furthermore, HFP is separated in the form of the third fraction. The method of the present embodiment can be carried out in a continuous manner, but it is not limited thereto and may be carried out in a batch-wise manner.

According to the present embodiment, the purity of HFPO in the first fraction can be, for example, about 90% by mole or more, and preferably about 99% by mole or more. The purity of HFP in the third fraction can be, for example, about 90% by mole or more, and preferably about 99% by mole or more.

The obtained third fraction may be returned to the reaction of forming HFPO from HFP, and thus HFP can be reused as the raw material (not shown). As shown in FIG. 1 with a dashed-dotted line, the fourth fraction may be supplied to the extractive distillation column 1 optionally together with a fresh solvent, and thus the solvent can be reused. The fourth fraction may include HFPO and HFP in a small amount. By returning the fourth fraction to the extractive distillation column 1 as described above, it is possible to recover HFPO and HFP in the fourth fraction without being wasted.

While one embodiment of the present invention was described above, the present invention is not limited to the above embodiment and various modifications can be made.

For example, the mixture and the solvent were separately supplied to the extractive distillation column in the above embodiment, but they may be supplied at the same time. Specifically, when the reaction of forming HFPO from HFP is carried out in a reaction solvent and this reaction solvent can also be used as the solvent for the extractive distillation operation, the mixture containing HFP, HFPO and the solvent (=reaction solvent) obtained after the reaction may be supplied to the extractive distillation column. Examples of the solvent which can also be used as the reaction solvent include HFC-365mfc, 1-bromopropane, 2-bromopropane and the like. Furthermore, in this case, the second fraction obtained by the extractive distillation operation may be returned to the reaction of forming HFPO from HFO without being subjected to the subsequent distillation operation, and thus HFP and the solvent can be reused as the raw material and the reaction solvent.

For example, it is not impossible to use, as the solvent, a fluorine-containing ether compound such as hydrofluoroether ($C_4F_9OCH_3$, $C_4F_9OC_2H_5$, $C_6F_{13}OCH_3$, $C_3HF_6$—$CH(CH_3)O$—$C_3HF_6$), perfluoroether or the like. However, its relative volatility of HFPO to HFP is low as compared with the above fluorine-containing compound or 1-bromopropane and 2-bromopropane.

EXAMPLES

Relative Volatility

With respect to cases using various solvents and no solvent, a relative volatility of HFPO to HFP was determined.

1) HFC-365mfc

In an Othmer-type vapor-liquid equilibrium measuring apparatus, 28 g of HFPO, 25 g of HFP and 495 g of HFC-365mfc ($CH_3CF_2CH_2CF_3$) as a solvent were respectively charged. When a liquid phase temperature was adjusted so that the pressure becomes 0.5 MPaG (gauge pressure), a liquid phase temperature was 71.8° C. After a lapse of 3 hours or more under the above conditions, a condensate liquid of the vapor phase portion and a liquid of the liquid phase portion were sampled, and these were respectively measured by a gas chromatograph. The molar ratio of HFP and HFPO was measured from the obtained data and the relative volatility of HFPO to HFP was determined as 2.67. These conditions and results are shown in Table 1.

2) 1-Bromopropane

The same procedures as in the case of the above (1) were carried out, except that the conditions were slightly changed while using, as a solvent, 1-bromopropane in place of HFC-365mfc, and the relative volatility of HFPO to HFP was determined. The conditions and results are shown in Table 1.

3) No Solvent

The same procedures as in the case of the above (1) were carried out, except that the conditions were slightly changed while using no solvent, and the relative volatility of HFPO to HFP was determined. The conditions and results are shown in Table 1.

4) Hydrofluoroether Under Trade Name of "HFE7200"

The same procedures as in the case of the above (1) were carried cut, except that the conditions were slightly changed while using, as a solvent, hydrofluoroether under the trade name of "HFE7200" ($C_4F_9OC_2H_5$, manufactured by 3M Company) in place of HFC-365mfc, and the relative volatility of HFPO to HFP was determined. The conditions and results are shown in Table 1.

5) Dichloromethane

The same procedures as in the case of the above (1) were carried our, except that the conditions were slightly changed while using, as a solvent, dichloromethane in place of HFC-365mfc, and the relative volatility of HFPO to HFP was determined. The conditions and results are shown in Table 1.

TABLE 1

| | | Charge amount | | | | | Rela- |
|---|---|---|---|---|---|---|---|
| No. | Solvent | HFP (g) | HFPO (g) | Sol-vent (g) | Pres-sure (MPaG) | Tem-perature (° C.) | tive vola-tility |
| 1) | HFC-365mfc | 25 | 28 | 495 | 0.5 | 71.8 | 2.67 |
| 2) | 1-bromopropane | 25 | 28 | 411 | 0.5 | 37.5 | 1.78 |
| 3) | None | 105 | 117 | — | 0.5 | 20.1 | 1.07 |
| 4) | HFE7200 | 25 | 28 | 883 | 0.5 | 65.3 | 1.16 |
| 5) | Dichloromethane | 25 | 28 | 284 | 0.5 | 23.5 | 1.42 |

Referring to Table 1, in the cases of using HFC-365mfC and 1-bromopropane as the solvent, a very high relative volatility was obtained as compared with the case of using no solvent. Therefore, it is understood that HFC-365mfc and 1-bromopropane are able to be preferably used as the solvent in the present invention. In contrast, in the cases of using HFE7200 and dichloromethane as the solvent, a very high relative volatility was not obtained as compared with the case of using no solvent.

Example

A case conducting the present invention in accordance with the Embodiment 1 described in the above with reference to FIG. 1 was simulated.

Extractive distillation was presumed to be carried out by continuously supplying a mixture of HFPO and HFP (in a molar ratio of 1:1) from the lower part of the concentration section at a rate of 106 g per hour to an extractive distillation column equipped with a solvent recovery section with about 7 plates, a concentration section with about 15 plates and a recovery section with 10 plates; continuously supplying HFC-365mfc as a solvent from the lower part of the solvent recovery section at a rate of 595 g per hour; continuously discharging a first fraction at a rate of 56 g per hour from the column top side while controlling a reflux ratio at 16; and continuously discharging a second fraction at a rate of 645 g per hour from the column bottom side. During the operation, the pressure in the extractive distillation column (in the system) was set at 0.2 MPaG (gauge pressure), and the column top temperature resulted in 0° C. and the column bottom temperature resulted in 59° C.

The molar fraction of HFPO in the first fraction obtained from the extractive distillation column resulted in 0.995. The first fraction resulted in containing 3 ppm by mole of the solvent.

On the other hand, the molar fraction of HFP in the second fraction obtained from the extractive distillation column resulted in 0.077, and a balance was substantially made off HFC-365mfc.

Recovery distillation was presumed to be carried out by continuously supplying the thus obtained second fraction to a solvent recovery column equipped with about 14 plates at the position of the 5th plate from the bottom at a rate of 645 g per hour; continuously discharging a third fraction at a rate of 50 g per hour from the column top side while controlling a reflux ratio at 10; and continuously discharging a fourth fraction at a rate of 595 g per hour from the column bottom side. During the operation, the pressure in the solvent recovery column (in the system) was set at 0.2 MPaG (gauge pressure), and the column top temperature resulted in −3° C. and the column bottom temperature resulted in 75° C.

The molar fraction of HFP in the third fraction obtained from the solvent recovery column resulted in 0.995 or more.

On the other hand, the molar fraction of HFC-365mfc in the fourth fraction obtained from the solvent recovery column resulted in 0.999 or more.

The obtained fourth fraction was presumed to be recycled to the extractive distillation column.

INDUSTRIAL APPLICABILITY

Hexafluoropropylene oxide separated by the method of the present invention can be used in the production of fluorine-containing compounds such as perfluorovinylether, and also can be used as a lubricating oil or a heating medium in the form of an oligomer.

REFERENCE SIGNS LIST

1 Extractive distillation column
3 Solvent recovery column

The invention claimed is:

1. A method for separating hexafluoropropylene oxide from hexafluoropropylene, which comprises subjecting a mixture including hexafluoropropylene oxide and hexafluoropropylene to an extractive distillation operation using, as a solvent, at least one of a fluorine-containing saturated compound selected from the group consisting of 1,1,1,3,3-pentafluoropropane; 1,1,1,3,3-pentafluorobutane; 1,1,1,2,2,3,4,5,5,5-decafluoropentane; and 1,1,2,2,3,3,4-heptafluorocyclopentane, and thereby separating the mixture into a first fraction including hexafluoropropylene oxide and a second fraction including hexafluoropropylene and the solvent.

2. The method according to claim 1, wherein the fluorine-containing saturated compound has a boiling point not less than −5° C. and not more than 100° C. under 0.1 MPa.

3. The method according to claim 1, which further comprises subjecting the second fraction obtained by the extractive distillation operation to a distillation operation thereby separating the second fraction into a third fraction including hexafluoropropylene and a fourth fraction including the solvent.

4. A method for separating hexafluoropropylene oxide from hexafluoropropylene, which comprises subjecting a mixture including hexafluoropropylene oxide and hexafluoropropylene to an extractive distillation operation using, as a solvent, at least one of 1-bromopropane and 2-bromopropane, and thereby separating the mixture into a first fraction including hexafluoropropylene oxide and a second fraction including hexafluoropropylene and the solvent.

5. The method according to claim 4, which further comprises subjecting the second fraction obtained by the extractive distillation operation to a distillation operation thereby separating the second fraction into a third fraction including hexafluoropropylene and a fourth fraction including the solvent.

* * * * *